US010494732B2

(12) United States Patent
Muglali et al.

(10) Patent No.: US 10,494,732 B2
(45) Date of Patent: Dec. 3, 2019

(54) METHOD FOR MONITORING THE TOTAL AMOUNT OF BRIGHTENERS IN AN ACIDIC COPPER/COPPER ALLOY PLATING BATH AND CONTROLLED PROCESS FOR PLATING (71) Applicant: Atotech Deutschland GmbH, Berlin (DE)

(72) Inventors: Mutlu-Iskender Muglali, Berlin (DE); Torsten Voss, Berlin (DE); Andreas Kirbs, Berlin (DE)

(73) Assignee: Atotech Deutschland GmbH, Berlin (DE)

( * ) Notice: Subject to any disclaimer, the term of this patent is extended or adjusted under 35 U.S.C. 154(b) by 0 days.

(21) Appl. No.: 16/090,597

(22) PCT Filed: May 17, 2017

(86) PCT No.: PCT/EP2017/061858
§ 371 (c)(1),
(2) Date: Oct. 2, 2018

(87) PCT Pub. No.: WO2017/198722
PCT Pub. Date: Nov. 23, 2017

(65) Prior Publication Data
US 2019/0078229 A1 Mar. 14, 2019

(30) Foreign Application Priority Data
May 19, 2016 (EP) ..................................... 16170304

(51) Int. Cl.
C25D 21/12 (2006.01)
C25D 3/38 (2006.01)
(Continued)

(52) U.S. Cl.
CPC ............... C25D 21/12 (2013.01); C25D 3/38 (2013.01); G01N 27/42 (2013.01); G01N 27/4166 (2013.01)

(58) Field of Classification Search
CPC ....................................................... C25D 21/12
See application file for complete search history.

(56) References Cited

U.S. PATENT DOCUMENTS 6,129,830 A 10/2000 Senge et al.
6,508,924 B1 1/2003 Gomez et al.
(Continued)

FOREIGN PATENT DOCUMENTS

EP 0402896 12/1990

OTHER PUBLICATIONS

Seunghoe Choe et al.; "High Accuracy Concentration Analysis of Accelerator Components in Acidic Cu Superfilling Bath", Journal of The Electrochemical Society, Jan. 1, 2016, pp. 33-39.
(Continued)

Primary Examiner — Brian W Cohen
(74) Attorney, Agent, or Firm — Renner, Otto, Boisselle & Sklar, LLP (57) ABSTRACT The present invention relates to a method for monitoring the total amount of brighteners in an acidic copper/copper alloy plating bath during a copper/copper alloy plating process, the use of such a method for controlling a plating process, a controlled process for electrolytically depositing copper/copper alloy onto a substrate utilizing the method for monitoring according to the present invention, and the use of one or more than one redox active compound for monitoring and/or determining the total amount of brighteners in the acidic copper/copper alloy plating bath.

15 Claims, 2 Drawing Sheets (51) Int. Cl.
*G01N 27/42* (2006.01)
*G01N 27/416* (2006.01)

(56) References Cited

U.S. PATENT DOCUMENTS

2005/0247577 A1   11/2005  Pavlov et al.
2011/0056840 A1*   3/2011  Isono .................... C25D 21/04
                                                                     205/296

OTHER PUBLICATIONS

PCT/EP2017/061858; PCT International Search Report and Written Opinion of the International Searching Authority dated Jul. 21, 2017.

* cited by examiner

METHOD FOR MONITORING THE TOTAL AMOUNT OF BRIGHTENERS IN AN ACIDIC COPPER/COPPER ALLOY PLATING BATH AND CONTROLLED PROCESS FOR PLATING

The present application is a U.S. National Stage Application based on and claiming benefit and priority under 35 U.S.C. § 371 of International Application No. PCT/EP2017/061858, filed 17 May 2017, which in turn claims benefit of and priority to European Application No. 16170304.6 filed 19 May 2016, the entirety of both of which is hereby incorporated herein by reference.

FIELD OF THE INVENTION

The present invention relates to the monitoring of brighteners in acidic copper/copper alloy plating baths.

In particular, the present invention relates to a method for monitoring the total amount of brighteners in an acidic copper/copper alloy plating bath during a copper/copper alloy plating process, the use of such a method for controlling a plating process, a controlled process for electrolytically depositing copper/copper alloy onto a substrate utilizing the method for monitoring according to the present invention, and the use of one or more than one redox active compound for monitoring and/or determining the total amount of brighteners in the acidic copper/copper alloy plating bath.

BACKGROUND OF THE INVENTION

In copper deposition processes deposition and bath properties are usually controlled and regulated by means of additives in the plating bath, including brighteners, levellers (sometimes also called boosters), and carriers (sometimes also called suppressors) (the terms "depositing" and "plating" are used interchangeably throughout the text).

Brighteners, also often called anti-suppressor additive or accelerator, are required to counter the suppressive effect of suppressor additives, which are common in such plating baths. A prominent brightener in acidic copper/copper alloy plating baths is bis-(sodium sulfopropyl)-disulfide (SPS). Typically, the total amount of brighteners in the bath during the deposition process is very low. However, such brighteners, among other additives, dramatically influence the copper deposition quality. As a result, the total amount of brighteners in a respective plating bath during the deposition process needs to be carefully monitored in order to maintain an optimal amount. This is challenging because the total amount usually continually varies due to (i) incorporation of said brighteners into the metal deposit,
(ii) degradation of said brighteners into break down products and
(iii) formation and accumulation of electrochemically active short life-time intermediate complexes in electrochemically aged baths binding and incorporating said brighteners.

Furthermore, the total amount of said brighteners in a plating bath is typically very low (1 to 100 ppm range) and thus, not accessible to each analytical tool.

In the art methods are described to monitor the total amount of brighteners and/or break down products in a respective plating bath.

US 2005/0247577 A1 discloses a method for measuring the concentration of an additive breakdown product in a plating bath for electrodepositing a metal. The breakdown product is 3-mercaptopropylsulfonic acid (MPS). The preferred method for monitoring is cyclic voltammetric stripping (CVS).

Choe et al. disclose in "High Accuracy Concentration Analysis of Accelerator Components in Acidic Cu Superfilling Bath", *Journal of The electrochemical Society*, 163 (2) D33-D39 (2016) a modified cyclic voltammetry stripping (CVS) method to measure the concentrations of bis-(sulfopropyl) disulphide (SPS) and 3-mercapto-1-propane sulfonate (MPS) in Cu plating solutions.

EP 0 402 896 A2 relates to a method of stabilising an organic additive in an acid copper electroplating solution.

U.S. Pat. No. 6,129,830 A concerns a process to electrolytically deposit copper layers within a short preparation time, especially in the manufacture of printed circuit boards.

U.S. Pat. No. 6,508,924 B1 discloses a method for determining the quantity of additive breakdown products in an electroplating bath.

According to our own experiences, methods known in the art frequently suffer from the disadvantage that they cannot be utilized to monitor the brighteners directly or often involve numerous steps to do so. As a result they are often very time consuming. It has been also frequently observed that in particular break down products and intermediates of any kind in a plating bath (i.e. in an electrochemically aged bath) negatively affect various common analytical tools by showing detrimental effects, such that no reliable results can be obtained (for further details about the detrimental effects see the text below).

OBJECTIVE OF THE PRESENT INVENTION

It was therefore a first objective of the present invention to provide a method for monitoring the total amount of brighteners in an acidic copper/copper alloy plating bath during a copper/copper alloy plating process that
  is easy to handle,
  provides results very quickly, such that a plating process can be constantly monitored,
  provides reliable results by minimizing the detrimental effects resulting from the interference of break down products and short life-time intermediate complexes with common analytical tools.

It was a second objective to provide a better controlled or more controlled copper/copper alloy deposition process.

SUMMARY OF THE INVENTION

The first objective of the present invention is solved by a method for monitoring the total amount of brighteners in an acidic copper/copper alloy plating bath during a copper/copper alloy plating process, the method comprising the steps:

(a) providing a plating bath sample from said plating bath, the plating bath comprising
  (a-1) one or more than one brightener selected from the group consisting of $$\text{-O}_3S\overset{}{\underset{n}{\frown}}S\overset{}{\underset{}{\frown}}S\overset{}{\underset{m}{\frown}}SO_3\text{-}, \quad HS\overset{}{\underset{m}{\frown}}SO_3\text{-},$$

$$\underset{S}{\overset{N}{\bigvee}}\text{-}S\overset{}{\underset{m}{\frown}}SO_3\text{-}, \quad (H_3C)_2N\overset{S}{\underset{}{\bigvee}}S\overset{}{\underset{m}{\frown}}SO_3\text{-},$$

-continued wherein
n and m are independently 1, 2, 3, 4 or 5, and
p is independently 0, 1 or 2,
(a-2) copper ions
(a-3) chloride ions,
(b) adding to the plating bath sample
  (b-1) one or more than one redox active compound, which is not a compound of (a-2), wherein said redox active compound
    exhibits a standard potential $E^0$ in the range of from −0.80 V to +1.45 V, and
    is selected from the group consisting of metal ions, metal oxide ions, iodide ions, and molecular oxygen,
  such that a measuring sample results,
(c) in a measuring unit comprising a working electrode, the working electrode being contacted with the measuring sample
  measuring a voltammetric or a chronoamperometric response of the working electrode by polarizing the electrode such that electrochemical current data are obtained,
(d) optionally processing the electrochemical current data obtained in step (c) in order to obtain processed electrochemical current data,
(e) comparing the electrochemical current data obtained in step (c) or the processed electrochemical current data obtained in step (d) with reference electrochemical current data or processed reference electrochemical current data.

Furthermore (as addressed in the second objective), deposition of copper/copper alloys can be better controlled by means of a controlled process for electrolytically depositing copper/copper alloy onto a substrate, the controlled process comprising the steps:
(A) providing the substrate and an acidic copper/copper alloy plating bath, wherein the plating bath comprises
  copper ions,
  chloride ions, and
  one or more than one brightener as defined in the method for monitoring according to the present invention (as defined above, preferably as defined as being preferred),
(B) contacting the substrate with the plating bath and applying a current such that copper/copper alloy is electrolytically deposited onto the substrate,
(C) while depositing, monitoring and/or determining the total amount of brighteners in the plating bath, utilizing the method for monitoring according to the present invention (as defined above or below, preferably as defined as being preferred),
(D) controlling the process for electrolytical copper/copper alloy deposition based on the result obtained in step (C).

DETAILED DESCRIPTION OF THE INVENTION

In our own experiments it has been shown that adding to the plating bath sample a redox active compound as defined above and below in the text (preferably as defined as being preferred) surprisingly solves the objectives of the present invention (see also Examples below and FIG. 1).

Throughout the text the term "independently" is used in combination with variables, e.g. in "n and m are independently 1, 2, 3, 4 or 5". This means that (i) the variable "n" is independent of the variable "m" in a brightener defined by "m" and "n", and (ii) in a mixture of for example two brighteners the variable "m" in the first brightener is independent of the variable "m" in the second brightener. As a result, the term means that different variables (e.g. "n" and "m") are independent of each other in the same compound and identical variables are independent of each other throughout different compounds (e.g. "n" in a first brightener and "n" in a second brightener).

If the term "copper plating bath" or "plating bath" (or a respective term) is used said terms also include copper alloys.

Throughout the text, the term "ppm" is based on weight, if not stated otherwise.

The term "during a copper/copper alloy plating process" includes the starting point of the plating process (i.e. plating process means depositing copper or copper alloy onto a substrate) and any point in time after the start of the plating process.

The copper plating bath contains copper ions, preferably in a concentration in the range of from 0.005 mol/L to 2 mol/L, preferably in the range of from 0.01 mol/L to 0.35 mol/L or from 0.36 mol/L to 1.5 mol/L, based on the total volume of the plating bath. The concentration of copper ions in the measuring sample is preferably in the range of from 0.8 to 1.2 mol/L, more preferably the concentration of copper ions in the plating bath sample and in the measuring sample is independently in the range of from 0.8 to 1.2 mol/L.

In the method according to the present invention the plating bath sample comprises chloride ions. A method for monitoring is preferred, wherein the plating bath sample comprises chloride ions in a total amount of 130 ppm or less, based on the total weight of the plating bath sample.

The term "adding to the plating bath sample" denotes an active action of adding the redox active compound as defined in step (b) to the plating bath sample. Preferably a subsequent/simultaneous mixing (e.g. stirring) of the plating bath sample is applied in order to dissolve the added compound at least partly. Thus, preferred is an "adding to and mixing with the plating bath sample", wherein the mixing is preferably a stirring. Preferably, the added redox active compound is fully dissolved in the measuring sample after adding, preferably after adding and mixing. The word "adding" in step (b) further denotes that the total amount of the redox active compounds (as defined in and for step (b) throughout the text) in the plating bath sample (which becomes the measuring sample) is increased after the addition compared to the total amount of said compounds in the plating bath sample prior to the addition. Preferably, the total amount is increased by a factor of at least two, preferably by a factor of at least 3, more preferably by a factor of 5 or more.

The term "redox active compound" refers to a compound being capable to participate in a redox reaction, either reduction or oxidation. Throughout the text, the redox active compounds utilized in step (b) do not involve: copper ions of any kind (component (a-2)), the brightener compounds (component (a-1)) as defined in step (a) and chloride ions (component (a-3)).

The term "standard potential" refers to a standard electrode potential based on the reference redox reaction $H_2 + 2H_2O \leftrightarrows 2H_3O^+ + 2e^-$ defined with 0.00 V at T=298 K.

In step (a) a plating bath sample is provided. Typically, the composition of the plating bath sample is identical with the plating bath for the point in time where the plating bath sample is obtained.

In step (b) the plating bath sample is modified by further steps. Further steps preferably include adding a solvent, a mixture of solvents or a base-composition in order to e.g. dilute the plating bath sample. A typical base-composition contains water as a solvent, copper ions, chloride ions, acids or bases (preferably to adjust and maintain a certain pH), complexing agents (e.g. tartrates), and further additives (e.g. surfactants, leveller and carrier compounds) but no brighteners (preferably no brighteners as defined in step (a) of the method of the present invention) and, thus, is identical to a freshly prepared plating bath with the exception that no brighteners are contained. If the plating bath sample is diluted compared to the plating bath, the dilution is preferably taken into account in step (e) or step (f) of the method for monitoring (for step (f) see the text below). Furthermore, prior to or after the measurement carried out in step (c), the base-composition itself is preferably electrochemically characterized utilizing the method for monitoring of the present invention.

The redox active compound added in step (b) is in some cases preferably added as a solid salt or solid compound (if the redox active compound exists as such), including suspensions. In other cases it is preferred to first fully or partly dissolve the redox active compound in an aqueous solvent, in a mixture of solvents or a base-composition (for the base-composition see the text above) in order to obtain said compounds in a (at least partially) dissolved form. Afterwards the plating bath sample is mixed with the redox active compound in such a (at least partially) dissolved form. This includes that the solvent, the mixture of solvents or the base-composition is prepared first (preferably already including the component (b-1)) and then the plating bath sample is added to it.

If the redox active compound is a gas, the gas is preferably directly purged into the plating bath sample and the measuring sample results. Optionally, the treated plating bath sample is further diluted as described above.

In a preferred method for monitoring according to the present invention (as defined above, preferably as defined as being preferred) the redox active compound (preferably $Fe^{2+}$ and/or $Fe^{3+}$) is dissolved in the undiluted plating bath sample. Subsequently, the plating bath sample including the redox active compound is diluted by mixing it with a base-composition (for the base-composition see the text above). As a result, a measuring sample as defined in step (b) is obtained. Any dilution factor is considered in step (e) and step (f).

Preferably, the redox active compound defined in step (b) (or as defined as being preferred) and added to and mixed with the plating bath sample according to step (b) is not contained in the plating bath. This means that the redox active compound is preferably an additional compound, only used for the utilization of the method for monitoring according to the invention.

Step (b) of the method for monitoring according to the present invention defines the step of "adding to the plating bath sample". This does not include contacting and/or mixing the plating bath sample with ambient air (natural, environmental unmodified air). In contrast, it includes adding to the plating bath sample molecular oxygen, wherein the molecular oxygen is a molecular oxygen containing gas, containing 80 Vol.-% or more molecular oxygen, preferably 90 Vol.-% or more, more preferably 95 Vol.-% or more, based on the total volume of the gas and determined at 20° C. and 1.0 bar. This includes for example adding to the plating bath sample technical oxygen gas (>99 Vol.-% molecular oxygen), which is in particular preferred in some cases. Our own experiments have shown that ambient air is insufficient to reliably modify the plating bath sample in a comparatively short time prior to the measurement step (c).

Preferred is a method for monitoring according to the present invention (as described above, preferably as described as being preferred), wherein said redox active compound
  exhibits a standard potential $E^0$ in the range of from −0.45 V to +0.79 V, and
  is selected from the group consisting of metal ions, metal oxide ions, iodide ions, and molecular oxygen, preferably is selected from the group consisting of metal ions, metal oxide ions, iodide ions, and molecular oxygen, more preferably is selected from the group consisting of metal ions, iodide ions, and molecular oxygen, most preferably is selected from the group consisting of metal ions and molecular oxygen and even more preferably is selected from the group consisting of metal ions.

More preferred is a method for monitoring according to the present invention (as described above, preferably as described as being preferred), wherein said redox-active compound is
  selected from the group consisting of iron ions, manganese ions, nickel ions, zinc ions, silver ions, iodide ions and molecular oxygen,
  preferably selected from the group consisting of $Fe^{2+}$, $Fe^{3+}$ and molecular oxygen, and
  more preferably selected from the group consisting of $Fe^{2+}$ and $Fe^{3+}$.

The above mentioned preferred ions exhibit a standard potential $E^0$ in the range of from −0.80 V to +1.45 V. More preferred metal ions exhibit a standard potential $E^0$ in the range of from −0.45 V to +0.79 V, such as iron ions.

In our own experiments it has been shown that satisfying results were obtained by utilizing redox-active compounds selected from the group consisting of iron ions, manganese ions, nickel ions, zinc ions, silver ions, iodide ions and molecular oxygen as defined above. Reliable and quick results have been observed by utilizing redox-active compounds selected from the group consisting of $Fe^{2+}$, $Fe^{3+}$ and molecular oxygen. These redox active compounds are widely available and comparatively inexpensive. Utilization of $Fe^{2+}$ and/or $Fe^{3+}$ is even more preferred because iron ions are simple to handle compared to gaseous redox active compounds such as molecular oxygen. Furthermore, iron ions as such are comparatively non-toxic. The term "$Fe^{2+}$ and $Fe^{3+}$" refers to free iron ions.

Preferably, the metal ions are added as common salts, preferably sulphates, phosphates, bromides, cyanides and chlorides, more preferably as sulphates, phosphates, bromides, and chlorides, most preferably as sulphates, phosphates, and bromides. More preferably, iron ions are added as iron(II)sulphate and iron(III)sulphate.

It is assumed that these redox active compounds "compensate" or "counteract" the detrimental effect of breakdown products in the measuring sample during the analysis carried out in step (c). However, the exact principle of operation is still not fully understood. On the basis of our experiments it has been shown that the benefit of the method for monitoring according to the present invention (as defined above, preferably as defined as being preferred) is the more obvious and impressive the longer the plating bath is in use, i.e. the more current per time unit has been applied to the plating bath and, thus, the more "aged" the plating bath is.

"Detrimental effect" means an unusual effect that has been observed in aged plating baths with respect to analytical results obtained in the absence of said redox active compounds. This unusual effect can be described as follows:

A freshly prepared acidic copper/copper alloy plating bath typically contains a defined total amount X of brighteners. It is assumed that this total amount decreases during the copper/copper alloy plating process due to incorporation and degradation of the brighteners. As a result, brighteners usually need to be added to the plating bath in order to maintain a comparatively constant total amount. However, according to our own experiments, the analytically determined total amount of brighteners in an aged plating bath, monitored by means of a voltammetric or a chronoamperometric response very often exceeded even the maximum total amount possible in the plating bath. It was observed that in many cases the determined total amount exceeded the maximum total amount by an order of magnitude, in a few cases even by two orders of magnitude. Interestingly, this detrimental effect intensively occurred if a respective plating bath sample was taken and immediately analysed, e.g. within 30 minutes after sample taking. However, if the respective plating bath sample is allowed to rest for 20 to 24 hours the detrimental effect disappears. This recovery process can be accelerated if the plating bath sample is stirred and ambient air is purged into it for a few hours. However, a recovery time of up to 24 hours or a treatment time of up to a few hours is unacceptably long and does not allow real time control of a respective plating process.

Surprisingly, if one or more than one redox active compound (as defined above, preferably as defined as being preferred) is added to the plating bath sample a reliable monitoring of the total amount of brighteners is possible within a few minutes with analytical tools that failed when utilized without adding redox active compounds to a respective plating bath sample.

Preferred is a method for monitoring according to the present invention (as described above, preferably as described as being preferred), wherein the one or more than one brightener comprises and/or , wherein n and m are independently 2, 3, or 4, preferably comprises wherein n and m are 3. If "n" and "m" are 3 the brightener is bis-(sodium sulfopropyl)-disulfide (SPS), which is one of the most popular and utilized brighteners in acidic copper plating baths. It is advantageous to use SPS because it well increases the deposition rate of copper by means of forming a Cu—I-3-Mercaptopropane sulfonic acid complex.

Preferably, the one or more than one brightener is selected from the group consisting of wherein n and m are independently 2, 3, or 4, more preferably the one brightener is bis-(sodium sulfopropyl)-disulfide (SPS).

Preferably, the total amount of brighteners in the plating bath sample (and in the measuring sample, respectively) is in the range of from 1 ppm to 100 ppm, based on the total weight of the plating bath sample.

As mentioned above in the text, the method for monitoring according to the present invention is in particular useful if the plating bath is considerably aged and used. According to our own experiments, the benefit of the method for monitoring according to the present invention was in particular obvious if the copper/copper alloy plating process was utilized with at least one soluble copper anode. Thus, a preferred method for monitoring according to the present invention (as described above, preferably as described as being preferred) is, wherein the acidic copper/copper alloy plating bath is utilized in the copper/copper alloy plating process with at least one soluble copper anode, before the plating bath sample is provided in step (a). Under such circumstances the method for monitoring according to the present invention provided excellent and very reliable results. During such a copper/copper alloy plating process the anode material of the soluble copper anode dissolves. It has been observed that breakdown products of soluble copper anodes and breakdown products of organic additives form complex aggregates. These aggregates, which are breakdown products in themselves, are considered to detrimentally influence common analytical tools, such as CVS and CPVS (the detrimental effect is explained in the text above).

The extent of soluble copper anode dissolution depends, among other factors, on the applied current density. The method for monitoring according to the present invention is in particular beneficial, if a high current density over a long period of time is applied without long idle times. In such cases much of the soluble copper anode is dissolved, and, typically, much of said complex aggregates are formed. Thus, a method for monitoring according to the present invention (as described above, preferably as described as being preferred) is preferred, wherein the acidic copper/copper alloy plating bath is utilized in the copper/copper alloy plating process for at least 5 Ah/L, based on the total volume of the acidic copper/copper alloy plating bath, more preferably for at least 10 Ah/L, most preferably for at least 15 Ah/L, before the plating bath sample is provided in step (a).

Preferably, the acidic copper/copper alloy plating bath is utilized in the copper/copper alloy plating process for at least 5 Ah/L per hour plating time, based on the total volume of the acidic copper/copper alloy plating bath, more preferably for at least 10 Ah/L per hour plating time, most preferably for at least 15 Ah/L per hour plating time, before the plating bath sample is provided in step (a).

According to our own experiments, the redox active compounds utilized in step (b) of the method for monitoring according to the present invention in particular counteract the detrimental effect of these breakdown products in a respective measuring sample.

The most preferred redox active compound is $Fe^{2+}$ and/or $Fe^{3+}$. In the method for monitoring according to the present invention both iron ion species can be utilized individually or in combination in step (b). Typically, an acidic copper/copper alloy plating bath utilized in a plating process with soluble anodes does not contain any iron ions. Such plating baths are preferred in the method for monitoring according to the present invention.

A method for monitoring according to the present invention (as described above, preferably as described as being preferred) is preferred, wherein the plating bath sample provided in step (a) comprises iron ions in a total amount of 0 to 50 ppm, preferably the plating bath sample provided in step (a) comprises reducible metal ions, which are not copper ions and tin ions, in a total amount of 0 to 50 ppm, based on the total weight of the plating bath sample. Preferably, the plating bath sample provided in step (a) comprises iron ions in a total amount of 0 to 30 ppm, more preferably the plating bath sample provided in step (a) comprises reducible metal ions, which are not copper ions and tin ions, in a total amount of 0 to 30 ppm, based on the total weight of the plating bath sample. Most preferably, the plating bath sample does not contain any iron ions. The term "reducible metal ions" denotes metal ions that could be reduced under corresponding conditions during the copper/copper alloy plating process to metallic metal being deposited onto the substrate.

If the plating bath or the plating bath sample contains iron ions in a total amount of 50 ppm or less, preferably 30 ppm or less (i.e. before step (b) is carried out), a counteracting or compensating effect on the basis of these iron ions was usually not or only insufficiently observed in our own experiments. In such cases a redox active compound (as defined above, preferably as defined as being preferred) has to be added as defined in step (b) of the method for monitoring according to the present invention. Throughout the text, the total amount of component (b-1) in the measuring sample is mentioned based on the amount of plating bath sample in the measuring sample, i.e. irrespective of a dilution of the plating bath sample. A method for monitoring according to the present invention (as described above, preferably as described as being preferred) is preferred, wherein the total amount of component (b-1) in the measuring sample is more than 50 ppm, based on the amount of plating bath sample in the measuring sample, preferably is 90 ppm or more, more preferably is 140 ppm or more, even more preferably is 200 ppm or more, most preferably is 400 ppm or more. If the plating bath comprises tin ions, preferably in a total amount of more than 10 ppm, a method for monitoring is preferred with the proviso that the total amount of component (b-1) as defined above does not include the amount of tin ions. Thus, it is in some cases preferred that the redox active compound does not comprise tin, more preferably does not comprise tin and zinc.

Even more preferred, the component (b-1) is $Fe^{2+}$ and/or $Fe^{3+}$, wherein the total amount of $Fe^{2+}$ and $Fe^{3+}$ in the measuring sample is more than 50 ppm, based on the amount of plating bath sample in the measuring sample, preferably is 90 ppm or more, more preferably is 140 ppm or more, even more preferably is 200 ppm or more, most preferably is 400 ppm or more. According to our own experiments, acceptable results have been already obtained if the total amount of component (b-1) in the measuring sample, based on the amount of plating bath sample in the measuring sample, is slightly above 50 ppm. Better results have been obtained if the total amount of component (b-1) in the measuring sample, based on the amount of plating bath sample in the measuring sample, is 90 ppm or more.

Preferably, the total amount of component (b-1) added to and mixed with the plating bath sample is 55 ppm or more, based on the total weight of the plating bath sample, preferably is 90 ppm or more, more preferably is 140 ppm or more, even more preferably is 200 ppm or more, most preferably is 400 ppm or more. Even more preferred, the total amount of $Fe^{2+}$ and $Fe^{3+}$ added to the plating bath sample is 55 ppm or more, based on the total weight of the plating bath sample, preferably is 90 ppm or more, more preferably is 140 ppm or more, even more preferably is 200 ppm or more, most preferably is 400 ppm or more. This is in particular preferred if the plating bath does not contain $Fe^{2+}$ and $Fe^{3+}$ or contains $Fe^{2+}$ and $Fe^{3+}$ only in a very low total amount, preferably below 10 ppm.

If molecular oxygen is used as redox active compound, the flow rate of oxygen containing gas per one ml plating bath sample is preferably at least 0.05 ml/min per 100 Vol.-% molecular oxygen. The treatment duration is preferably at least 300 seconds.

A method for monitoring according to the present invention (as described above, preferably as described as being preferred) is preferred, wherein at least 80 weight-%, preferably at least 90 weight-%, more preferably at least 95 weight-%, most preferably 100 weight-%, of the total amount of the redox active compounds as defined in (b-1) in the measuring sample is added in step (b). This is in particular preferred if the redox active compounds are selected from the group consisting of metal ions, metal oxide ions, iodide ions, and molecular oxygen.

Preferably at least 80 weight-%, preferably at least 90 weight-%, more preferably at least 95 weight-%, most preferably 100 weight-%, of the total amount of $Fe^{2+}$ and $Fe^{3+}$ ions in the measuring sample is added in step (b).

The plating bath is an acidic copper/copper alloy plating bath, wherein the pH of the plating bath is preferably 6 or less, more preferably 5 or less, most preferably 3 or less. It is preferred that also the measuring sample according to step (b) of the method for monitoring of the present invention has a pH of 6 or less, preferably of 5 or less, more preferably of 3 or less.

The temperature of the measuring sample while step (c) of the method for monitoring of the present invention is carried out is preferably in the range of from 15° C. to 35° C.

Our own experiments have shown that the compensation and counteraction, respectively, due to the redox active compound(s) added to the plating bath sample allows on the one hand very reliable analytical results. On the other hand the analytical analysis can be carried out very quickly. It appears that the positive influence of the redox active compounds quickly takes effect. A method for monitoring according to the present invention (as described above, preferably as described as being preferred) is preferred, wherein step (c) is started no later than 30 minutes after step (b) is completed, preferably no later than 10 minutes, more preferably no later than 5 minutes, most preferably no later than 2 minutes. Most preferably steps (a) to (c) of the method for monitoring according to the present invention are carried out in 30 minutes or less, preferably in 20 minutes or less.

It is possible (although not preferred) to carry out step (b) and to store a respective measuring sample for even up to 24 hours before carrying out step (c). Our own experiments have shown that such samples provide identical results compared to measuring samples analysed without delay in step (c).

Step (c) of the method for monitoring according to the present invention includes measuring a voltammetric or a chronoamperometric response of the working electrode by polarizing the electrode.

The measuring unit preferably comprises a three-electrode set-up (working electrode, reference electrode and counter electrode).

The working electrode is preferably selected from the group consisting of gold working electrode, platinum working electrode, stainless steel working electrode, copper working electrode, boron-doped diamond working electrode, and glassy carbon working electrode. Preferably, the working electrode is a platinum working electrode.

Differently shaped working electrodes can be used for the method for monitoring of the present invention including plate shaped electrodes, rings, ribbons, discs and wires.

Preferably, the working electrode is rotating and is preferably used for mixing in step (b) too. In some cases, the rotation speed for mixing in step (b) and measuring in step (c) is preferably identical. Preferably the rotation speed independently ranges in steps (b) and (c) from 500 to 5000 rpm, more preferably from 1500 to 4000 rpm, most preferably from 2000 to 3000 rpm. More preferably, the rotation speed is constant while the measurement is carried out in step (c).

Preferably, the reference electrode is a common commercially available reference electrode, preferably selected from the group consisting of Ag/AgCl reference electrode, $Hg/Hg_2Cl_2$ reference electrode, $Hg/HgC_4H_6O_4$ reference electrode, and $Hg/Hg_2SO_4$ reference electrode.

The counter electrode is preferably an inert electrode, preferably a stainless steel counter electrode or a noble metal counter electrode (a preferred noble metal counter electrode is a platinum counter electrode). In a few cases it is preferred that the counter electrode is separated from the measuring sample by a diaphragm. A preferred counter electrode is a stainless steel counter electrode.

Working electrodes used in the method for monitoring according to the present invention are preferably reused after a cleaning step, more preferably at least for a number of measurements. Such a cleaning step is essential in order to remove and desorb any deposit (e.g. oxides, sulphides, organic residues, grease, oils, and fingerprints) from the surface of the working electrode prior to a measurement according to step (c). Thus, preferred is a method for monitoring according to the present invention (as described above, preferably as described as being preferred) additionally comprising prior to step (c) the following step:
 cleaning the working electrode in a solution comprising one or more than one inorganic acid or one or more than one base, wherein the cleaning is preferably an electrochemical cleaning.

The above mentioned cleaning step always includes a chemical cleaning (effect of e.g. chemical etching by means of the inorganic acid or base). Preferably, the solution comprises sulfuric acid (preferably in a concentration of 0.2 to 1.0 M) or sodium hydroxide (preferably in a concentration of 0.04 to 0.4 M). However, preferably the chemical cleaning is combined with an electrochemical cleaning. In such a cleaning step the chemical cleaning is supplemented by electrolytic oxidation and reduction processes on the surface of the working electrode in order to oxidize and/or reduce any compounds deposited on the electrode's surface. It is believed that removal and desorption of said deposited compounds is improved upon oxidation and/or reduction. Our own experiments have shown in many cases that an electrochemical cleaning in an acidic solution (e.g. a 0.5 M $H_2SO_4$ containing cleaning solution) provides an optimal cleaning process. As a result, unnecessary costs for new working electrodes can be avoided. Typically, the electrochemical cleaning is monitored by voltammetry, preferably by cyclic voltammetry. Suitable conditions for voltammetry are for example: cyclic voltammetry, 100 mV/s.

Throughout the text the term "voltammetric response" denotes a current response recorded over time with linearly varying electrode potential.

The term "chronoamperometric response" denotes a current response recorded over time at a constant electrode potential.

The term "polarizing the electrode" denotes applying a defined overpotential versus the reference electrode (for the reference electrode see the text above).

A method for monitoring according to the present invention (as described above, preferably as described as being preferred) is preferred, wherein the response of the working electrode measured in step (c) is a voltammetric response by cyclic voltammetric stripping (CVS) or a chronoamperometric response by cyclic pulse voltammetric stripping (CPVS).

Preferably, the steps (a), (b) and (c) are carried out in the measuring unit.

Step (d) of the method for monitoring according to the present invention is an optional processing step. After step (c) electrochemical current data are obtained, which are "raw" data (e.g. a correlation of current vs. potential or time). Thus, the monitoring of the total amount of brighteners in the acidic copper/copper alloy plating bath is a correlation of (i) total amount of said brighteners and (ii) current data.

In the simplest case (although less preferred), the total amount of brighteners in an acidic copper/copper alloy plating bath can in some cases acceptably be monitored based on such unprocessed raw data derived from two measuring samples, wherein one measuring sample is a reference sample. Typically, the comparing according to step (e) of the method according to the present invention is used to supervise/control the acidic copper/copper alloy plating bath and/or the copper/copper alloy plating process (for further details see the text below regarding the controlled process).

In contrast, a method for monitoring according to the present invention is preferred (as described above, preferably as described as being preferred), wherein the raw data are processed in order to obtain processed data (i.e. processed electrochemical current data). A method for monitoring according to the present invention (as described above, preferably as described as being preferred) is preferred, wherein the processed electrochemical current data according to step (d) are selected from the group consisting of metal stripping peak area, metal stripping peak height, integrated current over a predetermined cathodic potential range, integrated current over an anodic potential range corresponding to metal stripping, and average current over a predetermined cathodic potential range.

On the basis of at least one reference sample containing a known total amount of brighteners (preferably two reference samples), not only the total amount of said brighteners in the acidic copper/copper alloy plating bath can be monitored but rather the total amount of said brighteners can be determined and converted into a concentration.

Preferred analytical techniques used to determine the concentration are "Linear Modified Approximation" (LAT) and "Modified Linear Approximation Technique" (MLAT), which have been introduced by R. Gluzman [Proc. 70$^{th}$ Am. Electroplaters Soc. Tech. Conf., Sur/Fin, Indianapolis, Ind. (June 1983)]. In such techniques, after a measuring sample was measured in step (c), typically known total amounts of brightener are added (brightener addition increment) in two or more than two increments to the measuring sample in order to obtain the respective number of reference samples (containing the unknown amount of brightener and the known added amount of brightener), wherein each reference sample is measured individually. Typically the added amount in each increment is identical.

Thus, preferred is a method for monitoring according to the present invention (as described above, preferably as described as being preferred) additionally comprising after step (e) the following step:
(f) based on the comparison in step (e), determining the total amount of the brighteners in the measuring sample.

In order to determine the total amount of brighteners in the measuring sample reference electrochemical current data or processed reference electrochemical current data obtained from reference measuring samples are used. Such reference samples contain known total amounts of brighteners.

Most preferred is a method for monitoring (as defined above, preferably as defined as being preferred) the total amount of brighteners in an acidic copper/copper alloy plating bath during a copper/copper alloy plating process, the method comprising the steps:
(a) providing a plating bath sample from said plating bath, the plating bath comprising (a-1)

wherein n and m is 3
(a-2) copper ions
(a-3) chloride ions,
wherein the total amount of iron ions in the plating bath sample is 0 to 30 ppm, based on the total weight of the plating bath sample, preferably is 0 to 5 ppm, more preferably is 0 ppm,
(b) adding to the plating bath sample
(b-1) one or more than one redox active compound, which is not a compound of (a-2), wherein said redox active compound
exhibits a standard potential $E^0$ in the range of from −0.80 V to +1.45 V, and
is selected from the group consisting of $Fe^{2+}$, $Fe^{3+}$ and molecular oxygen, preferably is $Fe^{2+}$ and/or $Fe^{3+}$,
such that a measuring sample results,
(c) in a measuring unit comprising a working electrode, the working electrode being contacted with the measuring sample
measuring a voltammetric response by cyclic voltammetric stripping (CVS) or a chronoamperometric response by cyclic pulse voltammetric stripping (CPVS), each by polarizing the working electrode such that electrochemical current data are obtained, preferably measuring a chronoamperometric response by cyclic pulse voltammetric stripping (CPVS),
(d) optionally processing (processing is preferred) the electrochemical current data obtained in step (c) in order to obtain processed electrochemical current data,
(e) comparing the electrochemical current data obtained in step (c) or (preferably) the processed electrochemical current data obtained in step (d) with reference electrochemical current data or (preferably) processed reference electrochemical current data.

Preferably, the above mentioned regarding the method for monitoring according to the present invention (in particular as defined as being preferred) applies likewise to this most preferred embodiment.

Figure 1:
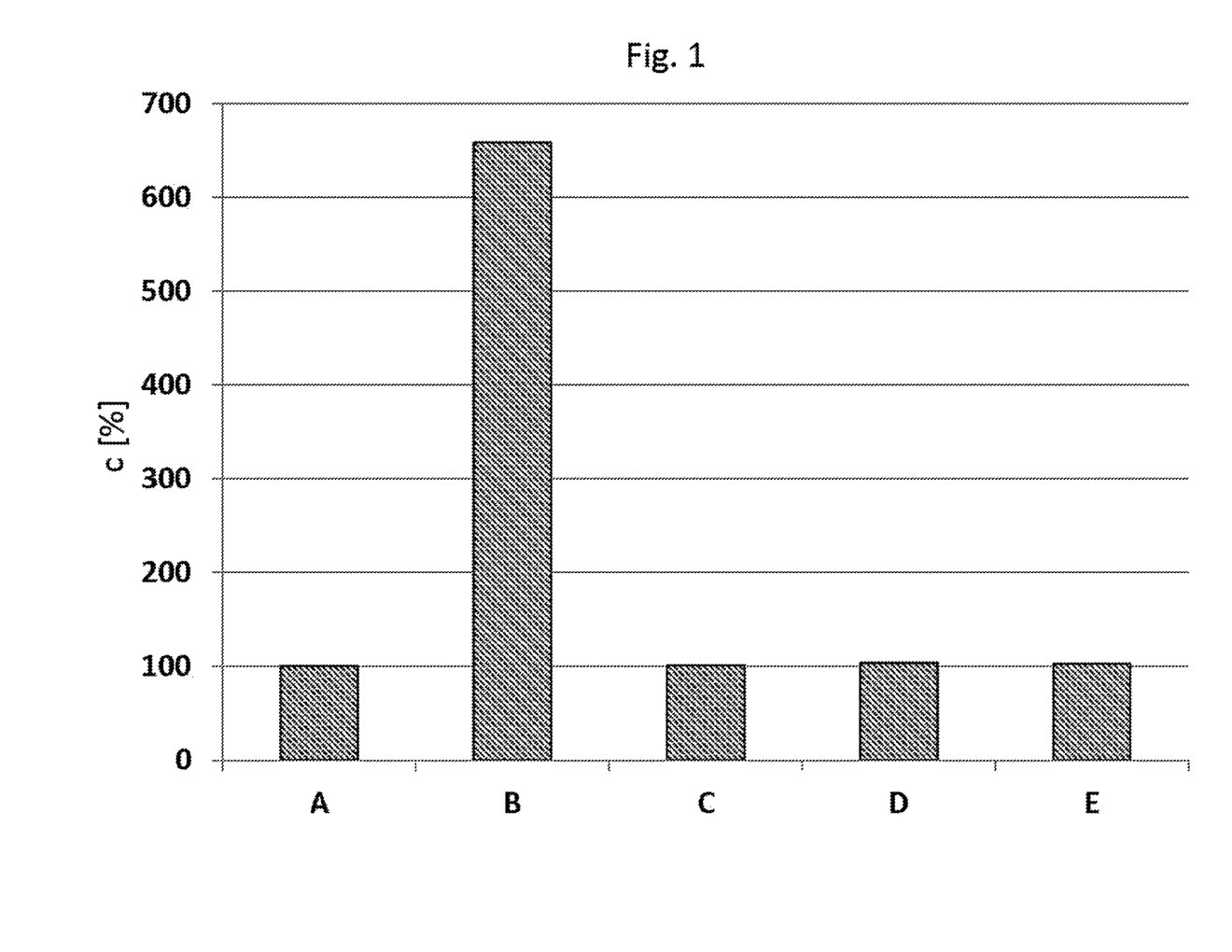
FIG. 1 shows a diagram, wherein on the y axis a relative amount of the brightener SPS is depicted (100% corresponds to the desired total amount in a respective plating bath). On the x axis analytical results are shown for a number of samples (more details in the text below and under "Examples")

In FIG. 1 experimental results are depicted for the following four samples (B, C, D, E) and the following reference sample (A):
A=sample of a freshly prepared plating bath containing a reference total amount of 100% SPS; the bath was not yet used in a plating process (i.e. it is a reference sample); the sample was analysed immediately after it was prepared and no redox active compound was added as defined is step (b) of the method according to the present invention; the analytically determined reference total amount of brightener is in agreement with the theoretical value;
B=sample of an aged/activated plating bath measured after 50 Ah/L within a few minutes after sample taking; no redox active compound was added as defined in step (b) of the method according to the present invention, nor any other treatment was applied;
C=sample of an aged plating bath after 50 Ah/L measured after being gently purged with ambient air for 14 hours; no redox active compound was added as defined in step (b) of the method according to the present invention;
D=sample of an aged plating bath after 50 Ah/L measured after 22 hours of rest/recovery; no redox active compound was added as defined in step (b) of the method according to the present invention and no ambient air was purged through the sample;
E=sample of an aged plating bath after 50 Ah/L measured after addition of 400 ppm $Fe^{3+}$, based on the amount of plating bath sample in the measuring sample; the sample was treated according to the method for monitoring according to the present invention; the over-all time for providing the plating bath sample, adding $Fe^{3+}$ (step (b)) and measurement (step (c)) was 3 to 5 minutes. The analytically determined total amount of SPS matches the expected total amount of SPS.

The concentration was determined for each sample by means of cyclic pulse voltammetric stripping (CPVS).

The method for monitoring according to the present invention usually allows an online monitoring of a copper/copper alloy plating process and thus a real time control (see the controlled process for electrolytically depositing copper/copper alloy in the text below). Thus, the present invention refers also to the use of the method for monitoring (as defined above, preferably as defined as being preferred) for controlling a copper/copper alloy plating process, preferably a copper/copper alloy plating process as described throughout the present text.

Preferred is the use of the method for monitoring (as defined above, preferably as defined as being preferred) for controlling a copper/copper alloy plating process by increasing or decreasing the concentration of brighteners as defined for the method for monitoring according to the present invention (preferably brighteners as defined as being preferred) in the acidic copper/copper alloy plating bath.

Preferably, the above mentioned regarding the method for monitoring according to the present invention (in particular as defined as being preferred) applies likewise to the use of the method for monitoring for controlling a copper/copper alloy plating process.

The result obtained after step (e) or (f) can be used in order to better control the respective copper/copper alloy plating process. Thus, the present invention refers also to a controlled process for electrolytically depositing copper/copper alloy onto a substrate, the controlled process comprising the steps:
  (A) providing the substrate and an acidic copper/copper alloy plating bath, wherein the plating bath comprises
    copper ions,
    chloride ions, and
    one or more than one brightener as defined for the method for monitoring according to the present invention (preferably brighteners as defined as being preferred),
  (B) contacting the substrate with the plating bath and applying a current such that copper/copper alloy is electrolytically deposited onto the substrate,
  (C) while depositing, monitoring and/or determining the total amount of brighteners in the plating bath, utilizing the method for monitoring according to the present invention (the method as described above, preferably as described as being preferred),
  (D) controlling the process for electrolytical copper/copper alloy deposition based on the result obtained in step (C).

The term "copper/copper alloy" denotes that either copper alone or a copper alloy is deposited.

In the controlled process according to the invention it is preferred that steps (C) and (D) are carried out repeatedly during the process for electrolytical copper/copper alloy deposition.

Preferably, the above mentioned regarding the method for monitoring according to the present invention (in particular as defined as being preferred) applies likewise to the controlled process for electrolytically depositing copper/copper alloy onto a substrate (the process as defined above, preferably the process as defined as being preferred).

Thus, preferred is a controlled process according to the present invention (as defined above), wherein in step (B) the applied current is at least 5 Ah/L, based on the total volume of the acidic copper/copper alloy plating bath, more preferably at least 10 Ah/L, most preferably at least 15 Ah/L.

In some cases a controlled process is preferred, wherein the applied current is at least 30 Ah/L or at least 40 Ah/L.

More preferred is a controlled process (the process as defined above, preferably the process as defined as being preferred), wherein in step (B) the applied current is at least 5 Ah/L per hour plating time, based on the total volume of the acidic copper/copper alloy plating bath, more preferably at least 10 Ah/L per hour plating time, most preferably at least 15 Ah/L per hour plating time.

In some cases a controlled process is preferred, wherein the applied current is at least 30 Ah/L per hour plating time or at least 40 Ah/L per hour plating time.

Preferred is also a controlled process (the process as defined above, preferably the process as defined as being preferred), wherein in step (B) at least one soluble copper anode is utilized.

The monitoring and/or determining according to step (C) can reveal that the total amount of brighteners in the copper plating bath is either below or above the target amount (set point). Typically, the total amount is below the target amount because said brighteners are usually incorporated into the deposited copper layer (or copper alloy layer) or degraded by oxidation/reduction processes during the deposition process. As a result, the total amount of said brighteners typically continually decreases in the copper plating bath during the copper plating process.

Therefore, brighteners are replenished after certain time intervals. However, in absence of an exact monitoring the replenishment can result in an overdosage of brighteners. As a result, the total amount of brighteners in the copper plating bath is above the target amount. Such an overdosage is unfavorable and usually results in undesired microcrystal structure formation in the metal deposit. In many cases the overdosage is compensated by diluting the copper plating bath, extracting or at least decreasing the total amount of organic additives by means of charcoal or consuming said organic additives by plating on dummy substrates ("dummy plating"). However, in each case the depositing process is delayed and additional costs are generated.

As mentioned above, it is preferred that steps (C) and (D) are carried out repeatedly, i.e. in cycles. In this case, a feedback signal is generated in step (C) of a cycle n+1 in response to an action taken in step (D) of cycle n. Such a feedback-response interaction is a preferred basis for a controlled process.

Thus, a controlled process is preferred (as described above, preferably as described as being preferred) wherein step (D) comprises the step:
  (D1) increasing the concentration of brighteners in the copper plating bath, preferably by adding said brighteners to the copper plating bath,
  or
  (D2) decreasing the concentration of brighteners in the copper plating bath, preferably as described above.

Preferred is a controlled process for electrolytically depositing copper/copper alloy onto a substrate, the controlled process comprising the steps:
  (A) providing the substrate and an acidic copper/copper alloy plating bath, wherein the plating bath comprises
    copper ions,
    chloride ions, and
    one or more than one brightener as defined for the method for monitoring according to the present invention (preferably brighteners as defined as being preferred),
  (B) contacting the substrate with the plating bath and applying a current such that copper/copper alloy is electrolytically deposited onto the substrate,
  (C) while depositing, monitoring and/or determining the total amount of brighteners in the plating bath, utilizing the method for monitoring according to the present invention (the method as described above, preferably as described as being preferred),
  (D) controlling the process for electrolytical copper/copper alloy deposition based on the result obtained in step (C), wherein step (D) comprises the step:
  (D1) increasing the concentration of the brighteners in the plating bath,
  or
  (D2) decreasing the concentration of the brighteners in the plating bath.

As a result, the method for monitoring according to the present invention and the controlled process for electrolytically depositing according to the present invention allows optimizing copper plating processes economically and ecologically.

Figure 2:
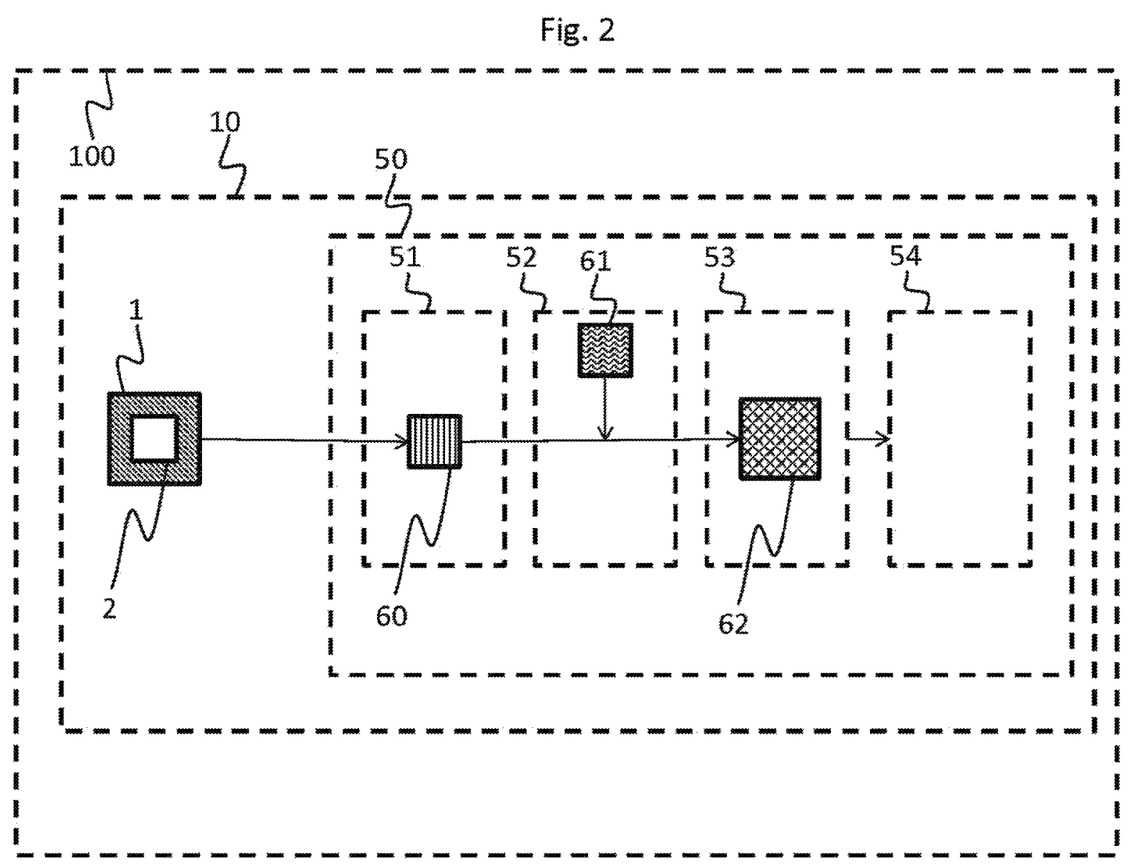
In FIG. 2 the method for monitoring according to the present invention and the controlled process according to the present invention are depicted schematically.

In FIG. 2 the controlled process of the present invention including the method for monitoring according to the present invention is schematically depicted.

In FIG. 2 processes (e.g. the method for monitoring according to the present invention) and process steps (e.g. providing, adding and mixing, etc.), respectively, are depicted in rectangular squares with dashed lines, wherein compositions (e.g. baths), compounds (e.g. iron ions) and samples (e.g. the plating bath sample) are depicted in rectangular squares with solid lines.

In FIG. 2 the controlled process (100) according to the present invention for electrolytically depositing copper/copper alloy onto a substrate (2) is depicted, including a copper/copper alloy plating process (10) and the method for monitoring according to the present invention (50).

The copper/copper alloy plating process (10) includes an acidic copper/copper alloy plating bath (1) and the substrate (2).

The method for monitoring according to the present invention (50) includes the following steps: (51), step (a): providing a plating bath sample; (52), step (b): adding a redox active compound; (53), steps (c) and (d): measuring a voltammetric or a chronoamperometric response to obtain electrochemical current data and optionally processing the electrochemical current data; (54), step (e): comparing the electrochemical current data with reference data.

Step (a) (51) includes the plating bath sample (60) obtained from the acidic copper/copper alloy plating bath (1).

Step (b) (52) includes adding to the plating bath sample (60) one or more than one redox active compounds (61).

Step (c) (53) includes the measuring sample (62), which is already obtained at the end of step (b) (not shown). However, the measuring sample (62) is investigated and analysed in step (c).

The present invention utilizes redox active compounds (compounds as defined above, preferably as defined as being preferred) in order to obtain reliable and quick results in the method for monitoring according to the present invention.

Thus, the present invention also refers to the use of one or more than one redox active compound (a compound as defined for the method for monitoring of the present invention, preferably as defined as being preferred), which is not a compound of (a-2), wherein said redox active compound
exhibits a standard potential $E^0$ in the range of from −0.80 V to +1.45 V, and
is selected from the group consisting of metal ions, metal oxide ions, iodide ions, and molecular oxygen,
in a plating bath sample of an acidic copper/copper alloy plating bath to obtain a measuring sample, for monitoring and/or determining the total amount of brighteners in the acidic copper/copper alloy plating bath, wherein the brighteners are selected from the group consisting of wherein
n and m are independently 1, 2, 3, 4 or 5, and
p is independently 0, 1 or 2,
preferably said brighteners are selected from the group of brighteners as defined throughout the text as being preferred.

This preferably means that the one or more than one redox active compound is used in the measuring sample of the plating bath sample of the acidic copper/copper alloy plating bath.

Preferably, the present invention refers to the use of one or more than one redox active compound (a compound as defined for the method for monitoring of the present invention, preferably as defined as being preferred), which are not copper ions, wherein said redox active compound
exhibits a standard potential $E^0$ in the range of from −0.80 V to +1.45 V, and
is selected from the group consisting of metal ions, metal oxide ions, iodide ions, and molecular oxygen,
in a measuring sample of a plating bath sample of an acidic copper/copper alloy plating bath, for monitoring and/or determining the total amount of brighteners in the acidic copper/copper alloy plating bath, wherein the brighteners are selected from the group consisting of wherein
n and m are independently 1, 2, 3, 4 or 5, and
p is independently 0, 1 or 2,
preferably said brighteners are selected from the group of brighteners as defined throughout the text as being preferred.

Preferably, the above mentioned regarding the method for monitoring according to the present invention (in particular as defined as being preferred) and regarding the controlled process according to the present invention (in particular as defined as being preferred) applies likewise to the use according to the present invention.

In particular preferred is a use (as defined above), wherein the one or more than one redox-active compound is selected from the group consisting of $Fe^{2+}$ and $Fe^{3+}$.

The present invention is illustrated by the following non limiting examples.

EXAMPLES

Sample Preparation:
In a first step an acidic copper plating bath (pH=<1) was prepared containing:
copper ions (50 g/L),
sulphuric acid (60 g/L), chloride ions (60 ppm), and
SPS 100% (reference total amount)

Furthermore, the above mentioned plating bath contains at least one further organic compound selected from the group consisting of leveller and carrier. A plating bath sample A (reference sample) was set aside (25 ml).

In a second step the copper plating bath was utilized in a copper plating process with the following parameters:
plating time: 2.5 h
plating current: 20 A
Cathode: Copper-foil (10 cm×10 cm), both sided plated,
Anode: two copper electrodes each doped with phosphorus (0.04-0.065 weight.-% phosphor) (plate form, 10 cm×10 cm each)
Test Tank: 3 L bath volume with spargers between anode and cathode
Bath convection rate: 50 L/h through an external pump
Bath Temperature: 30° C.

During the plating process SPS was added stepwise to maintain a basically constant SPS concentration in the plating bath. The added amount of SPS was based on empirical observations. SPS was replenished after every 10 Ah.

In a third step four further plating bath samples were separated (25 ml volume each, plating bath samples B, C, D, E.

In a fourth step plating bath samples A to E were modified to obtain measuring samples A to E.

Measuring Sample a (Reference Sample, FIG. 1, A):
Plating bath sample A (containing a known total amount of SPS, set point) was obtained prior to the start of the copper plating process and was not affected by any electrical current. 1 ml of the plating bath sample was mixed with 79 ml of a base composition (containing water, copper ions, sulfuric acid, chloride ions, and the at least one further organic compound) to obtain Measuring Sample A.

Measuring Sample B (FIG. 1, B):
Plating bath sample B was obtained after 50 Ah/L, which means that the copper plating bath was intensively used. No particular treatment was carried out with the sample, except that 1 ml of plating bath sample B was mixed with 79 ml of the base composition used for Measuring Sample A to obtain Measuring Sample B. Measuring Sample B was immediately measured by CPVS.

Measuring Sample C (FIG. 1, C):
Plating bath sample C was obtained after 50 Ah/L. Prior to CPVS measurement ambient air was gently purged through the plating bath sample for 14 hours with a gas flow rate of approximately 0.5 ml/min. Afterwards, 1 ml of treated plating bath sample C was mixed with 79 ml of the base composition used for Measuring Sample A to obtain Measuring Sample C.

Measuring Sample D (FIG. 1, D):
Plating bath sample D was obtained after 50 Ah/L. Prior to CPVS measurement the sample was allowed to rest/recover for 22 hours at ambient air. However, no ambient air was purged through the sample nor any other treatment was carried out, except that after the resting time 1 ml of said plating bath sample was mixed with 79 ml of the base composition used for Measuring Sample A to obtain Measuring Sample D.

Measuring Sample E (FIG. 1, E):
Plating bath sample E was obtained after 50 Ah/L and treated according to the method for monitoring according to the present invention. $Fe^{3+}$ ions were added to and dissolved in the plating bath sample. Afterwards, 1 ml of said plating bath sample was mixed with 79 ml of the base composition used for Measuring Sample A to obtain Measuring Sample E. After adding $Fe^{3+}$, the total amount of $Fe^{3+}$ in the plating bath sample was 400 ppm, based on the total amount of the plating bath sample (equals 400 ppm of $Fe^{3+}$ in Measuring Sample E, based on the amount of plating bath sample in the measuring sample). $Fe^{3+}$ was added as $Fe_2(SO_4)_3 \cdot 5H_2O$ in dissolved form, wherein the additional dilution of the plating bath sample was neglectable. Similar to Sample B, Measuring Sample E was prepared and measured expeditiously after plating bath sample E was collected from the test tank.

CPVS Measurement Parameters:
Working Electrode (WE): Pt (4 mm diameter)
Counter Electrode (CE): Stainless steel rod
Reference Electrode (RE): Ag/AgCl (0.1 M KCl); in the present text potentials are given with respect to the RE

| | |
|---|---|
| Mixing delay | 10 sec |
| Mixing rotation rate | 2500 rpm |
| Number of scans | 5 scans |
| Rotation rate | 2000 rpm |
| Plating | −0.10 V/15 s |
| Stripping | 0.36 V/10 s |
| Cleaning | 1.585 V/5 s |
| Solution volume | 80 ml |
| Dilution factor | 1:80 |
| Brightener addition increment | two brightener additions of known amounts |

Time interval between step (b) and step (c): 1 to 3 min
Measurement duration (step (c)): 10 to 15 min Results:
FIG. 1, sample B shows that after intensive use of an acidic copper plating bath the total amount of SPS in a respective sample cannot reliably monitored or determined immediately after the sample is obtained. In order to supress the detrimental effect of break down products in such a sample a time consuming recovery time of approximately 22 hours is needed (FIG. 1, sample D). However, as seen for Measuring Sample E, a sample treated in accordance with the method for monitoring according to the present invention allows an immediate analysis of such a sample without significant delay. Furthermore, reliable results are obtained. According to Measuring Sample E, the total amount of SPS in the sample corresponds to the expected total amount of SPS after empirical replenishment of SPS.

The detrimental effect typically occurring in such an aged bath was clearly observed as shown in FIG. 1, sample B. However, the detrimental effect can efficiently counteracted by utilizing the method for monitoring according to the present invention and as shown in FIG. 1, sample E.

Very similar reliable results have been obtained using (i) $Fe^{2+}$ ions and (ii) molecular oxygen gas (>99 Vol.-% molecular oxygen) purging gently through a respective sample with a flow rate of 5 ml/L for 300 seconds (data not shown).

The invention claimed is:

1. A method for monitoring the total amount of brighteners in an acidic copper/copper alloy plating bath during a copper/copper alloy plating process, the method comprising the steps:
   (a) providing a plating bath sample from said plating bath, the plating bath comprising
      (a-1) one or more than one brightener selected from the group consisting of wherein
n and m are independently 1, 2, 3, 4 or 5, and
p is independently 0, 1 or 2,
(a-2) copper ions, and
(a-3) chloride ions,
(b) adding to the plating bath sample
(b-1) one or more than one redox active compound, which is not a compound of (a-2), wherein said redox active compound
exhibits a standard potential $E^0$ in the range of from −0.80 V to +1.45 V, and
is selected from the group consisting of metal ions, metal oxide ions, iodide ions, and molecular oxygen,
such that a measuring sample results from steps (a) and (b),
(c) in a measuring unit comprising a working electrode, the working electrode being contacted with the measuring sample
measuring a voltammetric or a chronoamperometric response of the working electrode by polarizing the electrode such that electrochemical current data are obtained,
(d) optionally processing the electrochemical current data obtained in step (c) in order to obtain processed electrochemical current data,
(e) comparing the electrochemical current data obtained in step (c) or the processed electrochemical current data obtained in step (d) with reference electrochemical current data or processed reference electrochemical current data.

2. The method of claim 1, wherein said redox-active compound is
selected from the group consisting of iron ions, manganese ions, nickel ions, zinc ions, silver ions, iodide ions and molecular oxygen.

3. The method of claim 1, wherein the one or more than one brightener comprises wherein
n and m are independently 2, 3, or 4.

4. The method of claim 1, wherein the acidic copper/copper alloy plating bath is utilized in the copper/copper alloy plating process with at least one soluble copper anode, before the plating bath sample is provided in step (a).

5. The method of claim 1, wherein the plating bath sample provided in step (a) comprises iron ions in a total amount of 0 to 50 ppm, based on the total weight of the plating bath sample.

6. The method of claim 1, wherein the total amount of component (b-1) in the measuring sample is more than 50 ppm, based on the amount of plating bath sample in the measuring sample.

7. The method of claim 1, wherein step (c) is started no later than 30 minutes after step (b) is completed.

8. The method of claim 1, wherein the response of the working electrode measured in step (c) is a voltammetric response by cyclic voltammetric stripping or a chronoamperometric response by cyclic pulse voltammetric stripping.

9. The method of claim 1, wherein the processed electrochemical current data according to step (d) are selected from the group consisting of metal stripping peak area, metal stripping peak height, integrated current over a predetermined cathodic potential range, integrated current over an anodic potential range corresponding to metal stripping, and average current over a predetermined cathodic potential range.

10. A method for controlling a copper/copper alloy plating process, comprising carrying out the process of claim 1, further comprising increasing or decreasing the concentration of the brighteners in the acidic copper/copper alloy plating bath, following step (e).

11. Controlled process for electrolytically depositing copper/copper alloy onto a substrate, the controlled process comprising the steps:
(A) providing the substrate and an acidic copper/copper alloy plating bath, wherein the plating bath comprises
copper ions,
chloride ions, and
one or more than one brightener as defined in claim 1,
(B) contacting the substrate with the plating bath and applying a current such that copper/copper alloy is electrolytically deposited onto the substrate,
(C) while depositing, monitoring and/or determining the total amount of brighteners in the plating bath, utilizing the method for monitoring according to claim 1,
(D) controlling the process for electrolytical copper/copper alloy deposition based on the result obtained in step (C), wherein step (D) comprises the step:
(D1) increasing the concentration of the brighteners in the plating bath,
or
(D2) decreasing the concentration of the brighteners in the plating bath.

12. Controlled process according to claim 11, wherein in step (B) the applied current is at least 5 Ah/L per hour plating time, based on the total volume of the acidic copper/copper alloy plating bath.

13. Controlled process according to claim 11, wherein in step (B) at least one soluble copper anode is utilized.

14. The method of claim 1, wherein said redox-active compound is selected from the group consisting of $Fe^{2+}$ and $Fe^3$ and wherein the total amount of component (b-1) in the measuring sample is 200 ppm or more, based on the amount of plating bath sample in the measuring sample.

15. The method of claim 1, wherein the one or more than one brightener comprises wherein n and m are 3, and said redox-active compound is selected from the group consisting of $Fe^{2+}$ and $Fe^3$, and wherein the total amount of component (b-1) in the measuring sample is 400 ppm or more, based on the amount of plating bath sample in the measuring sample.

* * * * *